United States Patent [19]
Battist et al.

[11] Patent Number: 5,728,400
[45] Date of Patent: Mar. 17, 1998

[54] APPARATUS AND PROCESS FOR STRENGTHENING LOW DENSITY COMPRESSION DOSAGE UNITS AND PRODUCT THEREFROM

[75] Inventors: Gerald E. Battist, Reston; B. Arlie Bogue, Broad Run; Garry L. Myers, Reston, all of Va.

[73] Assignee: Fuisz Technologies Ltd., Chantilly, Va.

[21] Appl. No.: 743,221

[22] Filed: Nov. 5, 1996

Related U.S. Application Data

[60] Division of Ser. No. 276,244, Jul. 18, 1994, Pat. No. 5,616,344, which is a continuation-in-part of Ser. No. 259,496, Jun. 14, 1994, abandoned, and Ser. No. 259,258, Jun. 14, 1994.

[51] Int. Cl.$^6$ .................. A61K 9/20; A61K 9/46
[52] U.S. Cl. .................. 424/464; 424/441; 424/440; 424/466; 424/467
[58] Field of Search .................. 424/464, 441, 424/466, 467, 440

[56] References Cited

U.S. PATENT DOCUMENTS

| | | | |
|---|---|---|---|
| 4,215,104 | 7/1980 | Ullman et al. | 424/464 |
| 4,376,111 | 3/1983 | Tovey | 424/464 |
| 4,493,822 | 1/1985 | Tovey | 424/464 |
| 4,647,448 | 3/1987 | Tovey | 424/467 |
| 4,735,805 | 4/1988 | Ni et al. | 424/464 |
| 5,391,378 | 2/1995 | Sanderson | 424/464 |
| 5,464,632 | 11/1995 | Cousin et al. | 424/465 |
| 5,529,789 | 6/1996 | Lo | 424/473 |
| 5,616,344 | 4/1997 | Battist et al. | 424/486 |
| 5,648,033 | 7/1997 | Bogue et al. | 264/109 |
| 5,653,926 | 8/1997 | Bogue et al. | 264/120 |

*Primary Examiner*—Amy Hulina
*Attorney, Agent, or Firm*—Ronald J. Baron; Sandra M. Nolan

[57] ABSTRACT

The present invention is a process for forming a low density compression dosage unit to provide increased strength. The process of the present invention includes compacting under bi-level compaction pressure to provide a continuous-volume dosage unit which has a first volume defining an edge portion of the unit and a density which is greater than a density of a second volume defining a non-edge portion of the unit. The present invention also includes the product resulting from the process and apparatus used to make such units.

8 Claims, 8 Drawing Sheets

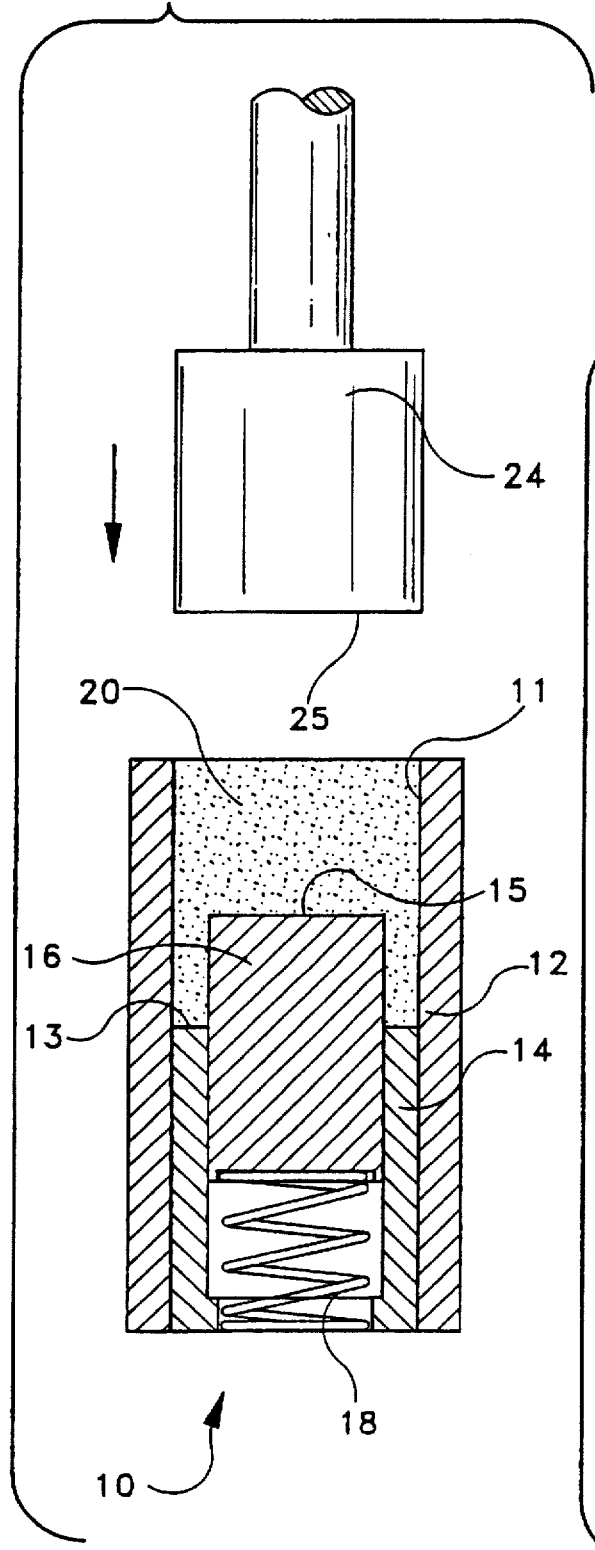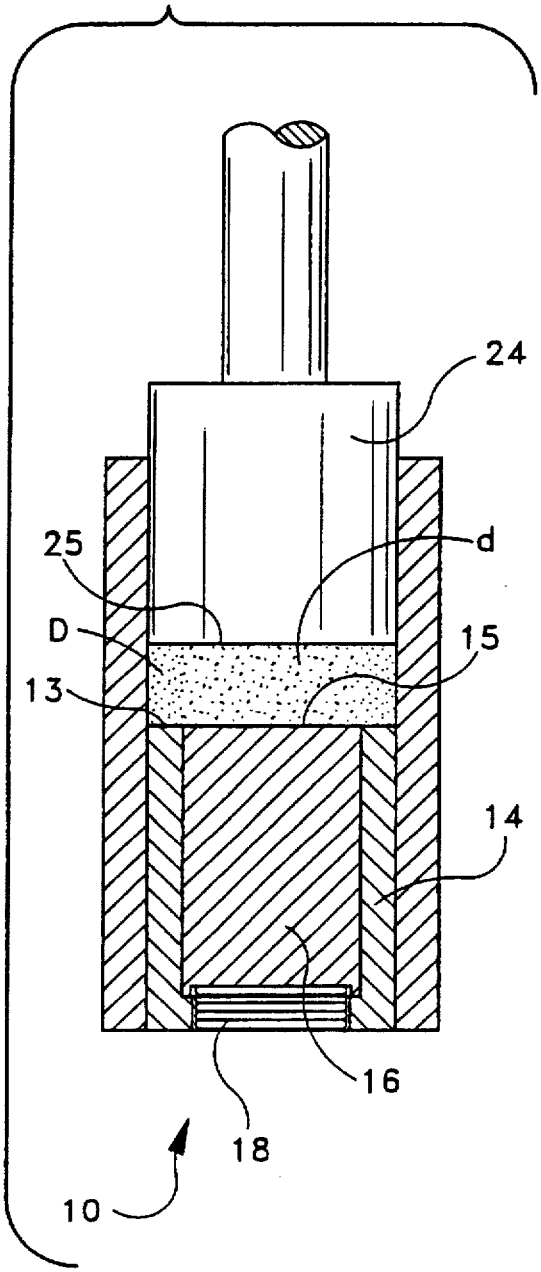

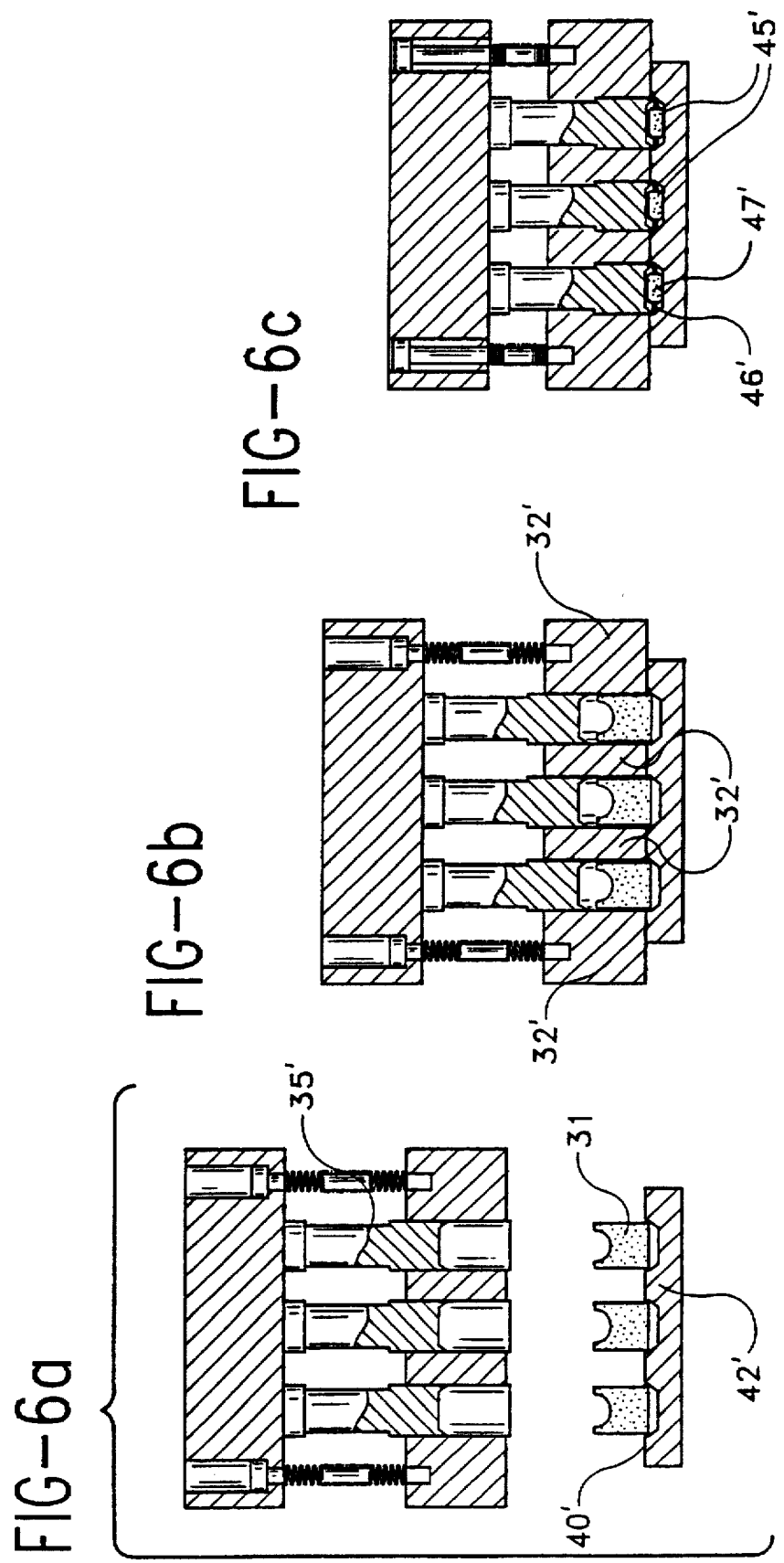

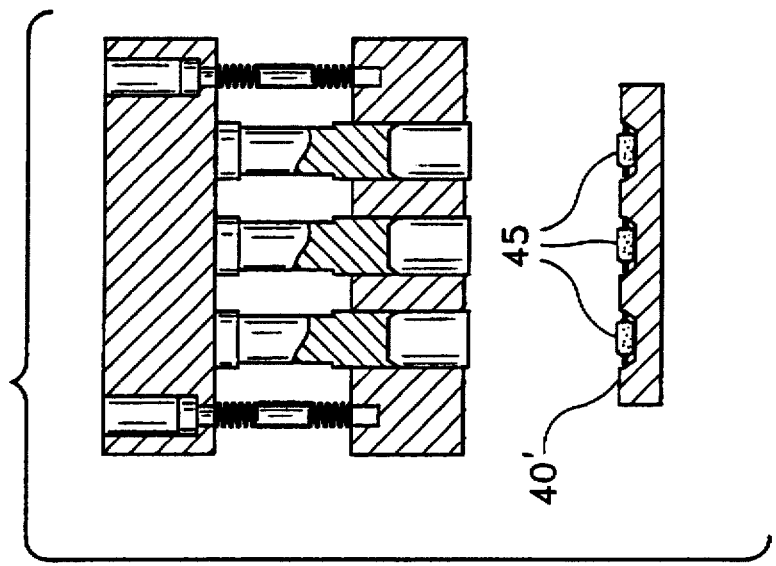
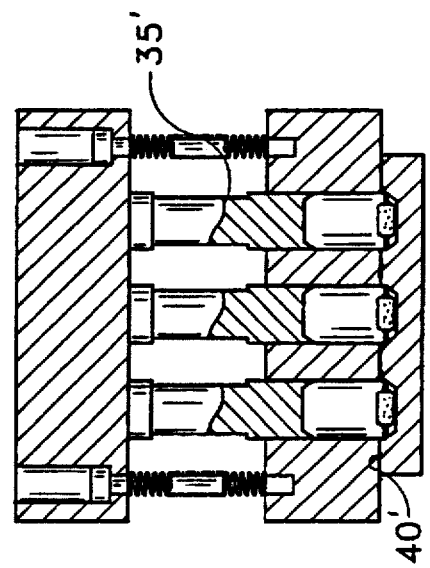

APPARATUS AND PROCESS FOR STRENGTHENING LOW DENSITY COMPRESSION DOSAGE UNITS AND PRODUCT THEREFROM

This is a divisional of application Ser. No. 08/276,244 filed on Jul. 18, 1994 now U.S. Pat. No. 5,616,344 which is a continuation-in-part of U.S. application Ser. No. 08/259,496 now abandoned, and U.S. application Ser. No. 08/259,258, pending, both of which were filed Jun. 14, 1994. The contents of each of these co-pending, commonly-owned applications is incorporated herein by reference.

BACKGROUND OF THE INVENTION

The present invention relates to compression dosage units, such as tablets, and more particularly relates to low density dosage units formed by compressing tabletting feedstock material.

Dosage units in the form of tablets are prepared by compressing a formulation containing a medicinal substance or drug and other ingredients, such as excipients selected for properties which enhance the production and use of the tablet. There are currently three known basic methods for preparing tablet granulations. These are wet granulation, dry granulation and direct compression. Both wet and dry granulations involve the formation of an agglomerate for feeding to a die cavity. Direct compression usually involves compressing a powder blend of an active ingredient with suitable excipients.

Other methods of preparing feedstock for preparing compression dosage units have been disclosed in copending, commonly owned U.S. application Ser. No. 08/194,682 filed Feb. 10, 1994 now U.S. Pat. No. 5,654,003, U.S. application bearing Attorney's Docket 447-105 and filed on Jun. 14, 1994, and U.S. application Ser. No. 08/259,258 pending, also filed Jun. 14, 1994. Each of these applications are incorporated herein by reference.

U.S. application Ser. No. 08/194,682 now U.S. Pat. No. 5,654,003 discloses a method of making a solid comestible by compressing shearform matrix masses sufficiently to form a comestible compression unit. The application bearing Attorney's Docket 447-105 discloses a method of preparing a quick dissolve comestible unit by mixing uncured shearform matrix and an additive, molding a unit dosage form therefrom, and curing the shearform matrix. Finally, U.S. application Ser. No. 08/259,258 pending discloses a method of preparing quick dissolve comestible units by initiating crystallization of shearform matrix, and combining, either before or after initiating crystallization, an additive with the shearform matrix to form flowable, compactible microparticulates. Finally, the micro-particulate medium is compacted to form the quick dissolve comestible unit. In each of these disclosures, the tabletting medium is prepared initially by use of shearform matrix. In most cases a quick dissolve tablet can be produced by providing a compressed body which is low density and capable of being disintegrated and dispersed relatively rapidly, and in many cases, instantaneously.

Tabletting processes known today in the art generally include the use of a machine which includes opposing punches and cavities into which a tabletting medium can be directed and subjected to compression between the punches. See, for example, U.S. Pat. Nos. 4,943,227, 4,880,373, 2,214,505, 2,068,619. Other references which discloses different shapes of dosage units are U.S. Pat. Nos. 4,493,822, 4,376,111, and an excerpt from The Consumer Guide for "Prescription Drugs," p. 194–208, Publications International, Ltd. (1990). None of the references cited above, however, show or suggest how to provide a low density dosage unit which has enhanced commercial value because of sufficient strength to be manufactured, disseminated, and sold in the appropriate commercial setting.

It is, therefore, an object of the present invention to overcome difficulties normally associated with low density compression units. Other objectives will also be apparent in view of the disclosure set forth herein.

SUMMARY OF THE INVENTION

The present invention is a process of forming a low density compression dosage unit, such as a tablet, in a manner whereby the strength is increased sufficiently for handling for packaging, distribution, and sales. The process includes compacting a continuous volume of tabletting-feedstock material under hi-level compacting pressure to provide a continuous-volume dosage unit. The dosage unit includes a first volume defining an edge portion of the unit which has a density greater than a density of a second volume which defines a non-edge portion of the unit. In preferred embodiments, the process of this invention is used to make tablets of the type disclosed in U.S. application Ser. No. 08/259,496 now abandoned and U.S. application Ser. No. 08/259,258 pending.

Preferably, the edge portion is less than about 50% of the continuous volume of the dosage unit, and most preferably is less than about 20% of the continuous volume. The edge portion circumscribes the non-edge portion and includes the perimeter surface, or edge surface, of the tablet.

With respect to the densities, the first volume at least about 10% greater than the density of the second volume, and preferably is at least about 15% greater than the density of the second volume.

In a preferred embodiment, the present invention is directed to a process for foxing a low density compression tablet by first providing a predetermined fixed mass of tabletting material and subjecting the fixed mass to sufficient compression to form a shaped object. The preformed material is then compacted under bi-level compacting pressure to provide a continuous volume dosage unit having a first volume defining an edge portion and with a density which is greater than the density of a second volume defining a non-edge portion of the unit. The preformed mass can have a substantially uniform density, and preferably the outer edge region can have a thicker cross section than a center region in order to provide a greater mass at the edge to increase the density of the final product. The tablet product can preferably have a center region which is greater in cross section than the outer edge portion.

In a most preferred embodiment of the present invention, the process as defined above can be conducted in a preformed plastic well having an inner region which is deeper than the outer edge portion and is in constant contact with the dosage unit during compaction.

Ideally, the process of the present invention is used to prepare pharmaceutical(s) for delivery by way of the compression dosage unit.

The present invention also includes the dosage unit itself as well as apparatus for manufacturing the dosage unit.

As a result of the present invention, low dosage compression unit such as tablets can be prepared which have the strength to be handled by machine or manually for packaging, distribution and sales. The term "strength" as used herein means the ability to withstand breakage, as well as significantly reduced friability.

These and other advantages of the present invention will be appreciated from the Detailed Description and Examples which are set forth herein. The Detailed Description and Examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein:

FIG. 1b is a top cross-section of the comestible unit shown in FIG. 1a;

FIG. 2a depicts the pre-compression condition of the feedstock material and apparatus of the present invention;

FIG. 2b depicts the condition of the feedstock and the apparatus during compression;

FIGS. 5a–5e show a preferred form of the process when utilizing a preform mass such as that shown in FIG. 4a;

FIGS. 6a–6e depict a preferred form of the process in accordance with the present invention using a preform mass such as that shown in FIG. 4b;

DETAILED DESCRIPTION OF THE INVENTION

Figure 1A:
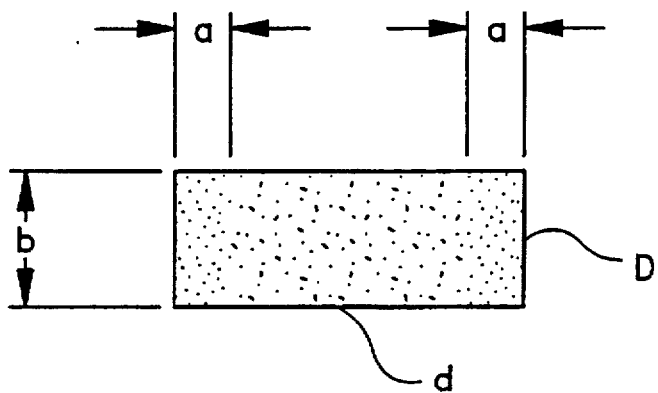
FIG. 1a is a side elevational cross-section of a dual density tablet prepared in accordance with the present invention.

The present invention is a unique process for preparing low density comestible units, such as tablets, and the units resulting therefrom. See FIGS. 1a and 1b. Tablets prepared in accordance with this invention have two portions, a lower density portion, d, which is centrally located, and a higher density portion, D, which surrounds the lower density portion and defines an edge portion of the tablet. The term "tablet" is used herein to mean a unit having two sides, sometimes referred to as a top and a bottom, and a continuous edge which joins the top and the bottom. The entire mass of the material throughout the tablet is the "volume" of the tablet.

The mass of the units prepared in accordance with the present invention is continuous in the sense that the feedstock material used to prepare the units is prepared in a single compression chamber defined by the surface of a die, and the faces of the compressor(s), sometimes referred to as "punches," but which has two different densities. A first volume is associated with the edge in that it circumscribes the unit and includes the edge surface. A second volume, which is referred to as the "non-edge" portion, is within the edge portion.

The non-edge portion of units prepared in accordance with the invention has a lower density, mass per unit volume, than the edge portion. The non-edge volume density is less than about 1.2 grams per cubic centimeter, preferably less than 0.8 grams per cubic centimeter, and most preferably not greater than 0.6 grams per cubic centimeter.

The edge portion of tablets prepared according to the invention have a higher density than the non-edge portion. The edge portion has a density which is at least about 10% greater than the density of the non-edge portion, preferably about 15% greater, and most preferably about 20% greater. Thus, if the density of the non-edge portion is about 0.6 grams per cubic centimeter, the density of the edge portion is preferably about 0.66 grams per cubic centimeter, preferably about 0.69 grams per cubic centimeter, and most preferably about 0.72 grams per cubic centimeter.

The extent of the edge portion is that amount of volume and surface sufficient to increase the "strength" of the unit for handling by processing machinery and personnel without deterioration of the unit. "Strength" includes both resistance to unit fracture and surface crumbling, i.e., friability.

A tabletting feedstock material which is particularly useful in the present invention is saccharide based. Particularly useful feedstocks for the tabletting process of this invention are disclosed in U.S. application Ser. No. 08/259,496 now abandoned and U.S. application Ser. No. 08/259,258 pending. In another embodiment, the feedstock disclosed in U.S. application Ser. No. 08/194,682 filed Feb. 10, 1994 now U.S. Pat. No. 5,654,003, which includes a free form agglomerate wherein selected ingredients such as a medicinal substance, and a carrier are fused together, is used in the process of the present invention. The free form agglomerate is distinguished from agglomerates formed from wet and dry granulations. The components of the tablet are thoroughly dispersed throughout the product because the mixture attained in the free form agglomerate is microstructurally stabilized against migration out of mixture. Fusion of the ingredients in a microstructurally-stabilized mixture is achieved prior to compression as a result of flash flow processing. The feedstock includes a saccharide-based material which acts as a carrier for the medicament.

The carrier material can be selected from material which is capable of undergoing both physical and/or chemical changes associated with flash-flow processing. Materials useful as matrices may be chosen from those carbohydrates which are capable of forming free-form agglomerates upon being processed. Maltodextrins are an example of such carrier materials. Maltodextrins include those mixtures of carbohydrates resulting from hydrolysis of a saccharide feedstock which are described as solids having a DE of less than 45.

The feedstock can also include maltooligo-saccharide produced by selective hydrolysis of cornstarch followed by removal of high and low molecular weight compounds. The general description of malto-oligosaccharides as contemplated herein is set forth in U.S. application Ser. No. 07/847,595 filed Mar. 5, 1992 now U.S. Pat. No. 5,387,431.

Other materials useful as matrices may be chosen from such classes as sugars or sugar derivatives. The term sugar is meant to include those carbohydrates having a high glucose profile. A high glucose profile means that the carbohydrate has a large number of six-carbon mono and disaccharides as well as other glucose-based oligomers. Mono-, di-, tri- and polysaccharides and their derivatives may be employed. Examples include glucose, sucrose, maltose, lactose, arabinose, xylose, ribose, fructose, mannose, pentose, galactose sorbose, dextrose, sorbitol, xylitol, mannitol, pentatol, maltitol, isomalt, sucralose and mixtures thereof.

Polydextrose is also contemplated or use as a carrier. Polydextrose is a non-sucrose essentially non-nutritive carbohydrate substitute. It an be prepared through polymerization of glucose in the presence of polycarboxylic acid catalyst and polyols. Generally, polydextrose is known to be commercially available in three forms: polydextrose A and polydetrose K, which are powdered solids, and polydextrose N supplied as a 70% solution. Each of these products also contain some low molecular weight components, such as glucose, sorbitol and certain oligomers. Regarding polydextrose, Applicants incorporate herein the contents of co-pending, U.S. application Ser. No. 07/881,612 filed May 12, 1992 now abandoned.

Other matrix materials include celluloses and starches and their chemical and biological derivatives. Celluloses, however, are generally added in combination with mono- and disaccharide-based materials because the celluloses are not as easily processed alone using flashflow techniques.

Flash-flow processing can be accomplished several ways. Flash-heat and flash-shear are two such processes which can be used. In the flash-heat process the feedstock material is heated sufficiently to create an internal flow condition which permits part of the feedstock to move at subparticle level with respect to the rest of the mass and exit openings provided in the perimeter of a spinning head. The centrifugal force created in the spinning head flings the flowing feedstock material outwardly from the head so that it reforms with a changed structure. Inasmuch as the medicinal substance can be present at the same time, the substance is fused to the feedstock material as it reforms so that it is substantially dispersed throughout the free-form agglomerate which is produced by the spinning head. The force necessary to separate and discharge flowable feedstock is only the centrifugal force which results in the spinning head. There is no compression whatsoever used to fuse the medicinal substance to the carrier.

In preferred embodiments, the flash-flow product can be mixed with other ingredients after flash flow processing. In U.S. application Ser. No. 08/259,496 now abandoned uncured shearform matrix is mixed with other ingredients, and in U.S. application Ser. No. 08/259,258 pending, the additional ingredients are added before or during crystallization.

One preferred apparatus for implementing a flash heat process is a "cotton candy" fabricating type of machine. The spinning machine used to achieve a flash-heat condition is a cotton candy machine such as the Econo-Floss Model 3017 manufactured by Gold Medal Products Company of Cincinnati, Ohio. Any other apparatus or physical process which provides similar forces and temperature gradient conditions can also be used.

In the flash-shear process, a shearform matrix is formed by raising the temperature in the feedstock material which includes a non-solubilized carrier, such as a saccharide-based material undergoes internal flow upon application of a fluid shear force. The feedstock is advanced and ejected while in internal flow condition, and subjected to disruptive fluid shear force to form multiple parts or masses which have a morphology different from that of the original feedstock.

The multiple masses are cooled substantially immediately after contact with the fluid shear force and are permitted to continue in a free-flow condition until solidified. The medicinal substance is fused to the carrier as it undergoes internal flow, disruption, and reformation as a free-form agglomerate. No compression whatsoever is used to effect fusion.

The flash shear process can be carried out in an apparatus which has means for increasing the temperature of a non-solubilized feedstock and means for simultaneously advancing it for ejection. A multiple heating zone twin screw extruder can be used for increasing the temperature of the non-solubilized feedstock. A second element of the apparatus is an ejector which provides the feedstock in a condition for shearing. The ejector is in fluid with the means for increasing the temperature and is arranged at a point to receive the feedstock while it is in internal flow condition. The ejector is preferably a nozzle which provides high pressure ejection of the feedstock material. See co-pending commonly-owned U.S. patent application Ser. No. 965,804 filed Oct. 23, 1992, now U.S. Pat. No. 5,380,473 entitled "Process For Making Shearform Matrix," which is incorporated herein by reference.

Medicinal substances which can be used in the present invention are varied. A non-limiting list of such substances is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, anti-diarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anticonvulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

Especially preferred active ingredients contemplated for use in the present invention are antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include aspirin, acetaminophen, and acetaminophen plus caffeine.

Other preferred drugs for other preferred active ingredients for use in the present invention include antidiarrheals such as immodium AD, antihistamines, antitussives, decongestants, vitamins, and breath fresheners. Also contemplated for use herein are anxiolytics such as Xanax; antipsychotics such as clozaril and Haldol; non-steroidal anti-inflammatories (NSAID's) such as Voltaren and Lodine; antihistamines such as Seldane, Hismanal, Relafen, and Tavist; antiemetics such as Kytril and Cesamet; bronchodilators such as Bentolin, Proventil; antidepressants such as Prozac, Zoloft, and Paxil; antimigraines such as Imigran, ACE-inhibitors such as Vasotec, Capoten and Zestril; Anti-Alzheimers agents, such as Nicergoline; and $Ca^H$-Antagonists such as Procardia, Adalat, and Calan.

The popular $H_2$-antagonists which are contemplated for use in the present invention include cimetidine, ranitidine hydrochloride, famotidine, nizatidine, ebrotidine, mifentidine, roxatidine, pisatidine and aceroxatidine.

The present invention can also be used to prepare veterinary products. Preferably, active ingredients useful for veterinary purposes can be included in the tabletting-feedstock material. Such ingredients will be known to those skilled in the art, and can include, but are not limited to, antibiotics, growth factor(s), vitamins, anti-inflammatory agents, etc.

Since a number of bio-affecting agents are heat sensitive, the present invention can include a process step of introducing heat sensitive agents at a point sufficiently proximal the flash-flow process step to reduce exposure of the heat sensitive to prolonged heat conditions. Thus, any heat sensitive agent can be incorporated into a carrier for subsequent ejection and formation of a shear-form matrix product.

In the alternative embodiments, heat sensitive components can be added after flash flow processing. Thus, heat is virtually eliminated from the tabletting aspect of production.

Another ingredient which can be included is an oleaginous material such as oleaginous liquid oleaginous flavor or aromatic oil as well as mineral oil, glycerin, polyethylene glycol, and the like. Examples of oleaginous liquids include, without limitation, vegetable oils, fish oils, lard, lanolin, cocoa butter and mixtures thereof. It will be appreciated that those hydrophobic materials which are solid at room temperature can be used provided they are rendered sufficiently liquid to be dispersed within a matrix during processing. Alternatively, in cases where the oleaginous material can be rendered dispersible with preheating without destroying or losing volatile components, such preheating can be employed.

Hydrogenated or partially hydrogenated vegetable oils are useful in the present invention and include materials such as corn oil, canola oil, cottonseed oil, sesame oil, soybean oil, grapeseed oil, sunflower oil, safflower oil, olive oil, peanut oil and the like.

Other materials which can be incorporated into the feedstock to enhance the shearform matrix include flavors and sweeteners (other than the carrier itself).

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combination thereof. A non-limiting representative list of examples includes citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral, i.e., alphacitral (lemon, lime), neral, i.e., beta-citral (lemon, lime) decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), and 2-dodecenal (citrus, mandarin), mixtures thereof and the like.

The sweeteners may be chosen from the following non-limiting list: glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof. Other sweeteners may also be used.

Other ingredients which may be included are fragrances, dyes, sweeteners both artificial and natural, and other additives for assisting in the tabletting process.

For example, fillers may be used to increase the bulk of the tablet to enable formulation to become suitable for compression. Some of the commonly used fillers are calcium sulfate, and di- and tri basic, starch, calcium carbonate, microcrystalline cellulose, modified starches, lactose, sucrose, maintol, and sorbitol.

Other ingredients includes binders which contributes to the ease of compression and general quality of the tablet. Binders include starches, pregelatinized starches, gelatin, polyvinylpyrrolidone, methylcellulose, sodium carboxymethylcellulose, ethylcellulose, polyacrylamides, polyvinyloxoazolidone, and polyvinylalcohols.

Lubricants are also useful in tabletting formulations in order to ease the ejection of the tablet from the die and to prevent sticking of the tablets to the punches and excess wear on dies and punches. Lubricants can include, but are not limited to, the following: magnesium stearate, calcium stearate, zinc stearate, hydrogenated vegetable oils, sterotex, polyoxyethylene, monostearate, talc, polyethyleneglycol, sodium benzoate, sodium lauryl sulfate, magnesium lauryl sulfate and light mineral oil.

Furthermore, disintegrants can be used to enhance the breakability of the compressed tablet in an aqueous environment. The disintegrants can include starch, alginic acid, guar gum, kaolin, bentonite, purified wood cellulose, sodium starch glycolate, isoamorphous silicate, and microcrystalline cellulose.

Another ingredient useful in tabletting are glidants which add to the cohesive matters in order to enhance flow properties by reducing interparticle friction. Glidants which can be used include starch, talc, magnesium and calcium stearate, zinc stearate, dibasic calcium phosphate, magnesium carbonate, magnesium oxide, calcium silicate, and silica aerogels.

Color additives useful in preparing tablets include food, drug and cosmetics (FD&C) colors, drug and cosmetic (D&C) colors, or external drug and cosmetic (Ext. D&C) colors. These colors are dyes, their corresponding lakes, and certain natural and derived colorants. Lakes are dyes absorbed on aluminum hydroxide.

In a preferred embodiment, the present invention is particularly useful in preparing antacid tablets. Antacids are conveniently provided in a rapid dissolving tablet form to provide a convenient method of delivering antacid to the consumer. The rapidly dissolving form provides an advantage in that the tablet is broken up into granules and mixed with saliva before swallowing. This renders the tablet antacid formulation a suspension. Active antacid ingredients include but are not limited to the following, including combinations thereof: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts. In a preferred embodiment, the antacid is a combination of calcium carbonate and magnesium hydroxide or magnesium carbonate.

Yet a further embodiment of the present invention includes the use of an effervescent disintegration agent. Its action can aid in the masking of objectionable taste of active ingredients such as vitamins, medicines and/or minerals, etc. It is generally believed that the positive organoleptic sensation achieved by the effervescent action in the mouth, the texture, speed and sensation of disintegration aids in masking undesirable flavor notes in the mouth.

In preferred embodiments of the present invention, the effervescent disintegration agent may include at least one acid selected from the group consisting of citric acid, tartaric acid, malic acid, fumaric acid, adipic acid, succinic acid, acid anhydrides and acid salts and mixtures thereof, and at least one base selected from the group consisting of carbonate salts, bicarbonate salts and mixtures thereof.

Inasmuch as the term effervescent refers to those agents which evolve gas, the bubble or gas generating the action is most often the result of the reaction of a soluble acid source and an alkali metal carbonate or carbonate source. The reaction of these two general classes of compounds produces carbon dioxide gas upon contact with water included in saliva. Carbonate sources include dry solid carbonate and bicarbonate salts such as sodium bicarbonate, sodium carbonate, potassium bicarbonate and potassium carbonate, magnesium carbonate and sodium sesequicarbonate, sodium glycine carbonate, L-lysine carbonate, arginine carbonate and amorphous calcium carbonate. While the food acids can be those indicated above, acid anhydrides of the above-described acids may also be used. Acid salts may include sodium, dihydrogen phosphate, disodium dihydrogen pyrophosphate, acid citrate salts and sodium acid sulfite. Other source of effervescence can be included and the present invention is not limited to those specifically set forth herein.

Also as previously mentioned, the ingredients of the effervescent agent can be included in one of at least three different ways. The first method includes incorporating the entire effervescent agent in the feedstock which is used to form the shearform product. The second manner of incorporating an effervescent disintegrating agent is to include the entire agent as an additive which is mixed with shearform matrix after it is formed. The third method contemplates incorporating one portion of the disintegrating agent in the shearform matrix and another portion of the disintegrating agent as an additive after formation of the shearform matrix material. The artisan will determine the best way to preserve the agent for its disintegrative and effervescent properties upon ingestion by the host.

Referring to the drawings, the process of the present invention can be described.

Referring to FIG. 2a and 2b, processing steps are shown which utilize a bi-level compaction apparatus 10. Referring to FIG. 2a, the feedstock 20 has already been introduced to a compression cavity which is bounded by the inside surface 11 of a die 12. Interior of the die 12 is located a spacer bushing 14, having a top surface 13, which surrounds a movable pre-tensioned punch 16. The punch 16 has been pre-tensioned by a compression spring 18. The punch 16 is movable with respect to the stationary bushing 14.

Finally, the device also includes a compression punch 24 having a compression surface 25 which forms the top wall of the compression chamber.

In operation, the lower punch 16 remains stationary until the compressor 24 acts on the feedstock 20 with sufficient force to compress the feedstock and, consequently, the spring 18. At the bottom of the downward compression stroke, which is shown in FIG. 2b, the lower punch 16 is shown in the fully compressed condition wherein the spring 18 has been fully compressed so that the top surface 15 of the punch 16 is substantially co-planar with the top surface 13 of the bushing 14.

When the chamber has been filled with feedstock material 20, the amount of material occupying the vertical space between the bushing 14 and the top of the chamber is greater than that occupying the vertical space between the face of punch 15 and the top of the chamber. Accordingly, at the end of the compression stroke shown in FIG. 2b, the amount of compressed material per unit volume in the surrounding or edge portion of the resulting unit is greater than the material compressed between compressor 24 and movable punch 16. Consequently, the density in the edge portion is greater than the density in the non-edge portion.

Figure 1B:
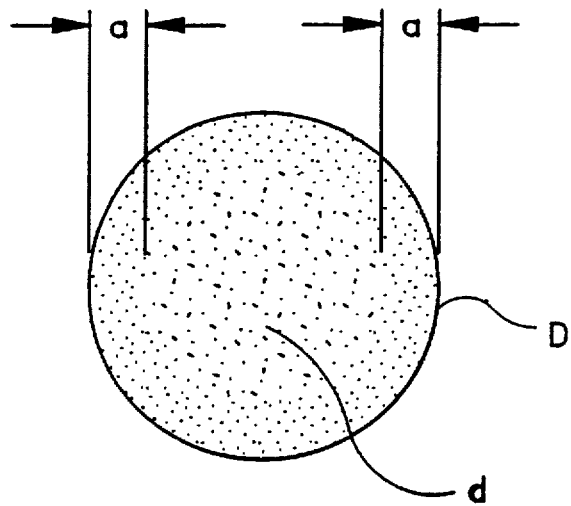

The resulting product is shown in FIG. 1a and 1b.

Figure 3:
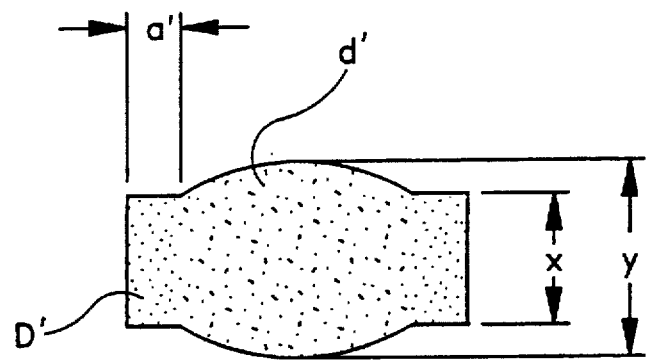
FIG. 3 shows an alternative embodiment of a dual density tablet prepared in accordance with the present invention.
Figure 4A:
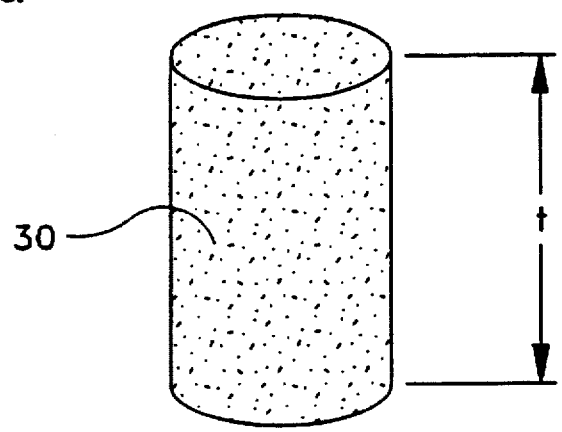
FIGS. 4a and 4b show preformed masses of tabletting material prior to compaction.
Figure 4B:
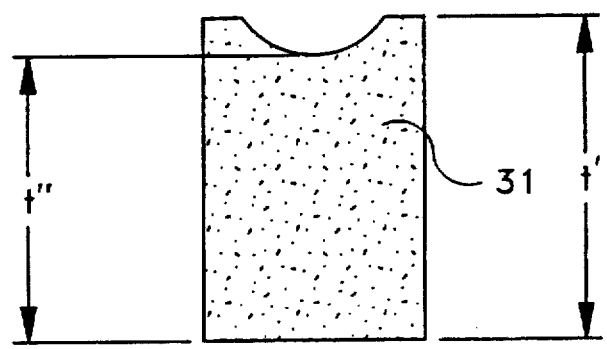

An alternative embodiment is shown in FIG. 3 wherein the edge portion is shown to have a cross-section, x, which is smaller than the greatest portion of the cross-section of the non-edge portion, y. Different configurations can be provided to the tablet in order to achieve different results, such as aesthetics, etc.

Yet a further embodiment of the process and the products described herein has been shown with reference to FIGS. 4a through FIG. 8. These alternative preferred embodiments include the use of a preformed mass of tabletting material. The preformed mass is prepared by providing a predetermined mass of tabletting material and subjecting it to sufficient compression to form a shaped object such as the cylinder 30 shown in FIG. 4a and the cylinder 31 shown in FIG. 4b. The cylinder 30 shown in FIG. 4a has a substantially uniform density and has an overall thickness t which is constant. In FIG. 4b, the preformed mass 31 has a substantially uniform density, but has a thickness t' at the outer edge which is less than the thickness t'' found in the interior portion of the cylinder. Either of these preformed masses can be used with great convenience in the manufacturing process of the present invention.

Referring then to FIGS. 5a–5e, the use of the preform mass 30 to prepare a product according to the inventive process has been depicted. One additional feature which is shown in FIGS. 5a–5e is the use of a preformed plastic tray 40 in which the preformed masses 30 have been provided for bi-level compaction in accordance with the present invention.

Figure 5C:
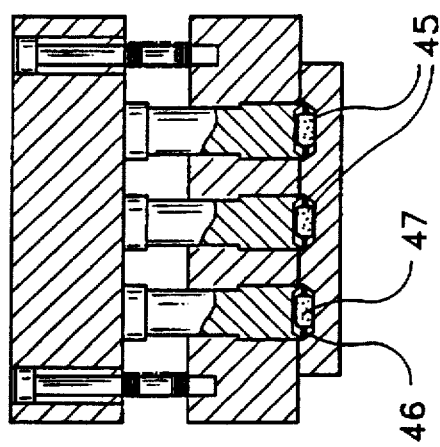
Figure 5B:
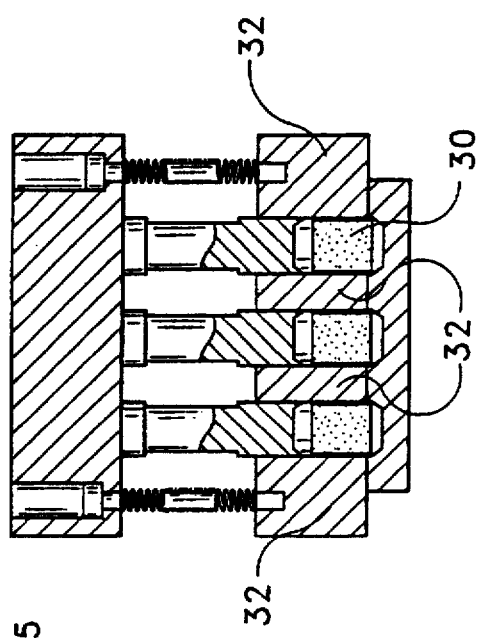
Figure 5A:
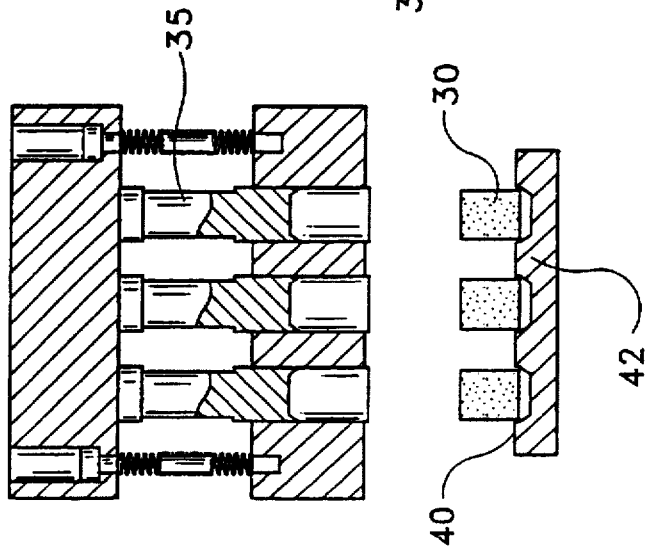
Figure 5E:
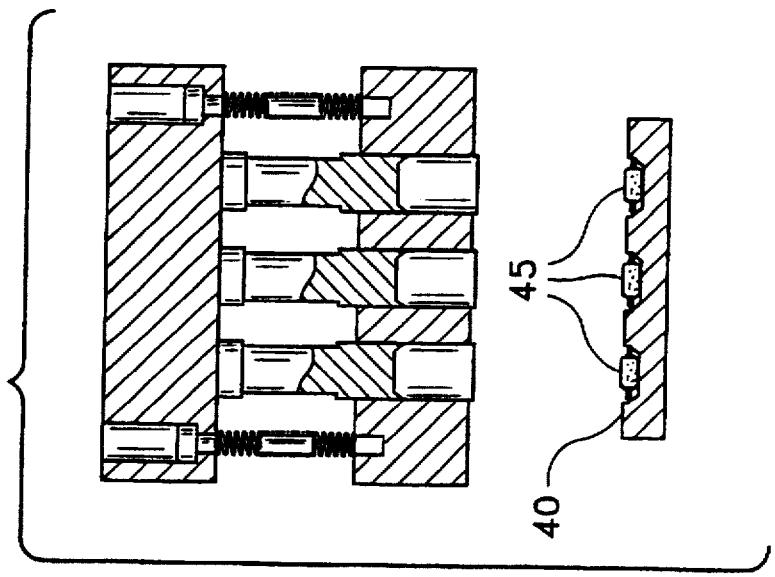
Figure 5D:
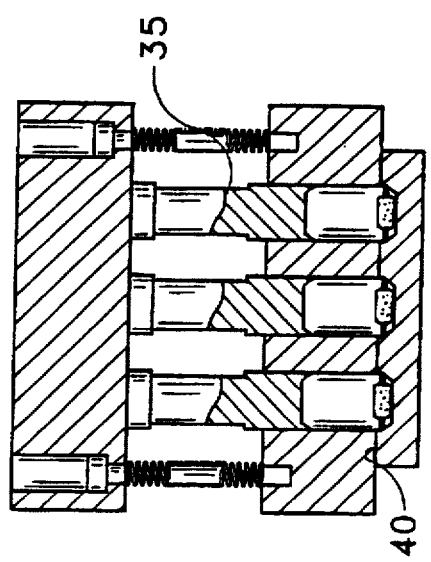

Referring to FIG. 5a, a series of compressors 35 are shown over preform tabletting masses 30 held in place by plastic package 40, which, in turn, is supported by support 42. In the next step shown in FIG. 5b, the compressors 35 are lowered over the preform masses 30 and are simultaneously confined in die members 32. FIG. 5c shows the compaction stroke wherein the compressors 35 are lowered against the masses 30 to form bi-level compaction units 45. It is noted that the edge portions 46 are of higher density than the non-edge portions 47. In FIG. 5d, the compressors 35 have been withdrawn leaving the product units in the tray 40. In FIG. 5e, the entire compaction unit has been raised above the completed product in its product tray for further processing. Further processing usually includes overlaying the product tray 40 with a protective covering, such as a metallic and/or plastic layer, which prevents deterioration by force and/or environmental conditions.

Referring to FIGS. 6a–6e, the same procedure is depicted using the preform mass 31. As a result of an increase thickness at the edge portions of the perform mass 31, the artisan is able to obtain yet a greater density at the edge portion 46' after compaction. Each of the steps and members shown in FIGS. 6a–6e have been given numbers previously assigned in FIGS. 5a–5e, except that each has been designated with a prime to show the similarity of the step or mechanical part.

Figure 7:
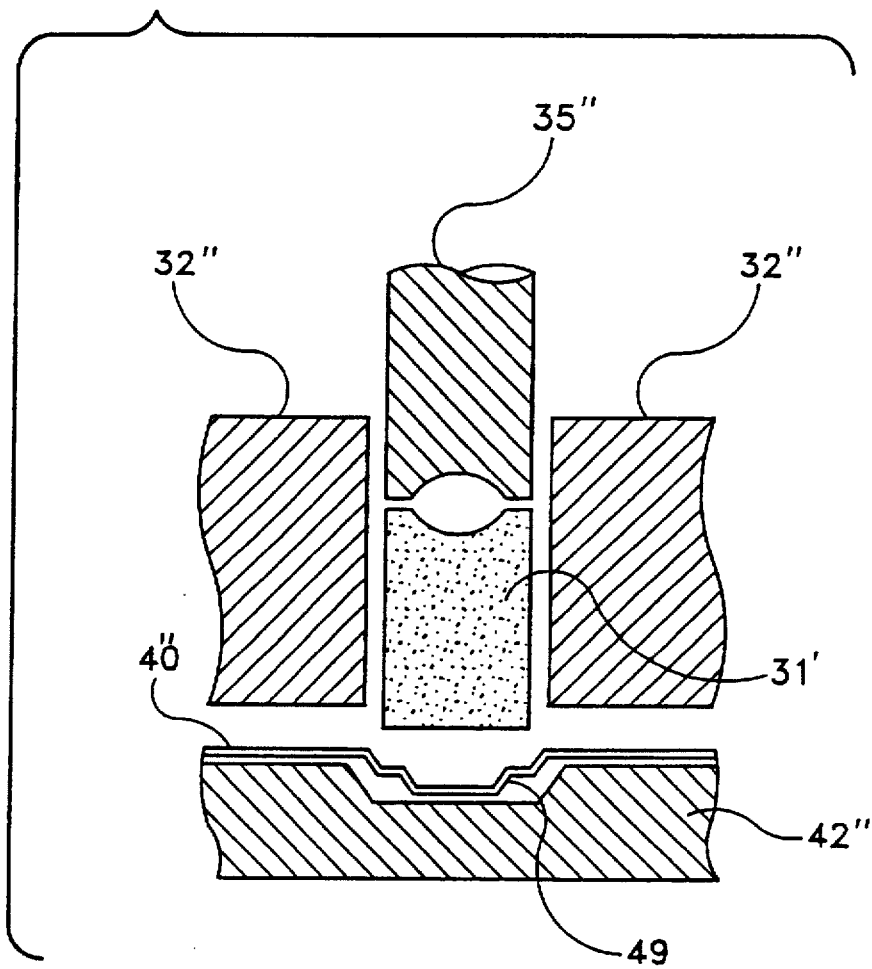
FIG. 7 is a detailed representation of a preferred form of the process shown in FIGS. 6a–6e.

Referring to FIG. 7, greater detail has been given to the procedure generally shown in FIGS. 6a–6e. The preformed plug 31' is shown directly over the well in product tray 40 which rests on support 42". The portions of the dye which capture the perform 31' is shown by walls 32". The bi-level compacting compressor 35" is shown during its downward stroke against preform tabletting mass 31'. A "step" 49 is shown in the well of product tray 40". The "step" 49 adds yet another design feature which enhances the ability to form the bi-level compaction unit having a greater density on the edge portion.

Figure 8:
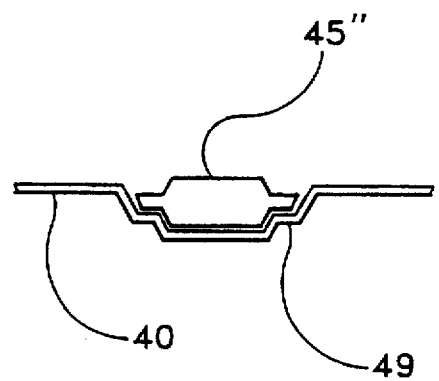
FIG. 8 is a schematic which depicts a most preferred form of the product after processing and before preparation for distribution and sales.

Referring to FIG. 8, a schematic is shown of the completed product unit 45" in the product tray 40 after the procedure has been completed. Once again, the step 49 is shown as providing another way to enhance the bi-level compaction capabilities of the process and the product 45" resulting therefrom.

EXAMPLE

The process of the present invention has been found to be particularly useful when producing a product from feedstock which has been described in U.S. application bearing Attorney's Docket 447-105. In this example, a rapid or quick dissolve comestible unit was prepared by mixing uncured shearform matrix containing a crystallization enhancer and an additive.

The mixture was then molded under a bi-level compacting pressure to provide a continuous volume dosage unit having a first volume defining and edge portion of the unit which was greater than the density of a second volume which defines a non-edge portion of the unit. The molded unit was then cured by subjection to environmental conditions of heat, moisture, and pressure which induce crystallization. Specifically, the unit was inserted in a sealed package and crystallization occurred over a period of time due to a critical amount of moisture in the unit, which was less than 5% by weight. The temperature can be controlled to achieve crystallization in very short periods or periods such as a week.

The units resulting from this process had a non-edge density of about 0.65 gram per cubic centimeter. The tablets were able to be handled manually and subjected to machinery for feeding into packages for commercial distribution and sales. The units resisted breaking and resisted crumbling. Thus, the process of the present invention significantly enhanced the capability of commercializing the product which was prepared therefrom.

Thus, while there have been described what are presently believed to be preferred embodiments of the present invention, those skilled in the art will realize that other and further modifications and changes can be made without departing from the true spirit of the invention, and it is intended to include all such further changes and modifications as come within the scope of the invention.

What is claimed is:

1. A low density compression dosage unit comprising:
   a continuous body prepared from a predetermined fixed mass of tableting material and compacted under bi-level compacting pressure to form a first portion and a second portion, said first portion defining an edge volume of said tableting material and having a first density, and said second portion defining a non-edge volume of said tableting material and having a second density, wherein said first portion and said second portion are the same material, said first density being greater thin said second density, whereby the strength of said unit is increased and the friability of said unit is decreased as compared to a low density unit formed under a single low density compaction pressure.

2. The compression dosage unit as defined by claim 1, wherein said edge volume is not more than about fifty percent (50%) of said continuous body of said about unit.

3. The compression dosage unit as defined by claim 1, wherein said first density is at least about ten percent (10%) greater than said second density.

4. A compression dosage unit as defined by claim 3, wherein said first density is at least about fifteen percent (15%) greater than said second density.

5. The compression dosage unit as defined by claim 1, which comprises a medicinal substance selected from the group consisting of antitussives, antihistamines, decongestants, alkaloids, mineral supplements, laxatives, vitamins, antacids, ion exchange resins, anticholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, antihypertensive drugs, vasoconstrictors, migraine treatments, antibiotics, tranquilizers, anti-psychotics, antitumor drugs, anticoagulants, antithrombotic drugs, hypnotics, antiemetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropcietic drugs, antiasthmatics, cough suppressants, mucolytics, anti-uricemic drugs and mixtures thereof.

6. The compression dosage unit as defined by claim 5, wherein said medicinal substance is selected from the group consisting of ibuprofen, acetaminophen, $H_2$ antagonists, aspirin, and combinations thereof.

7. The compression dosage unit as defined by claim 5, wherein said medicinal substance is an antacid selected from the group consisting of aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono- or dibasic calcium phosphate, tricalcium phosphate, potassium bicarbonate, sodium tartrate, sodium bicarbonate, magnesium aluminosilicates, tartaric acids and salts and combinations thereof.

8. The compression dosage unit as defined by claim 7, wherein said antacid is selected from the group consisting of calcium carbonates, magnesium hydroxide, and combinations thereof.

\* \* \* \* \*